United States Patent [19]

Schwan et al.

[11] 4,099,009
[45] Jul. 4, 1978

[54] 1-(4-CHLOROPHENYL)-3-(1-UREIDO)-2-IMIDAZOLIDINONE

[75] Inventors: Thomas J. Schwan; Ralph L. White, Jr., both of Norwich, N.Y.

[73] Assignee: Morton-Norwick Products, Inc., Norwich, N.Y.

[21] Appl. No.: 786,465

[22] Filed: Apr. 11, 1977

[51] Int. Cl.$^2$ .......................................... C07D 233/48
[52] U.S. Cl. ................................. 548/319; 424/273 R
[58] Field of Search ......................................... 548/319

[56] References Cited

U.S. PATENT DOCUMENTS

| 2,746,960 | 5/1956 | Geuer et al. | 548/319 |
|---|---|---|---|
| 2,776,979 | 1/1957 | Michels | 548/319 |
| 3,115,499 | 12/1963 | Michels | 548/319 |
| 3,859,301 | 1/1975 | Wat | 548/319 |

OTHER PUBLICATIONS

Reimlinger et al., Chem. Ber. 1971, vol. 104, pp. 3947–3954.
Rabinowitz et al., Chem. Abst. 1969, vol. 70, No. 87771u.

*Primary Examiner*—Natalie Trousof
*Attorney, Agent, or Firm*—Anthony J. Franze

[57] ABSTRACT

The compound 1-(4-chlorophenyl)-3-(1-ureido)-2-imidazolidinone is useful as a gastric acid antisecretory agent.

1 Claim, No Drawings

1-(4-CHLOROPHENYL)-3-(1-UREIDO)-2-IMIDAZOLIDINONE

This invention is concerned with the compound 1-(4-chlorophenyl)-3-(1-ureido)-2-imidazolidinone.

This compound has utility in inhibiting gastric acid output and thus is useful as a medicinal agent. It exhibits a salutary effect upon gastric acid secretion. Such effect is evidenced using a modified standard pylorus-lighted secretory testing procedure in the rat. Sprague-Dawley rats, weighing 180–210 g and previously fasted for 24 hours, were used. The compound was given perorally as suspensions in 0.5% carboxymethyl cellulose 1 hour prior to pylorus ligation. Under light ether anesthesia, the rat stomach was ligated at the pylorus region. Four hours after ligation the conscious rat was sacrificed by a chloroform overdose. The stomach was carefully excised and its content drained into a centrifuge tube. Samples were centrifuged to separate secretions from debris. Gastric fluid volume reading and determination of sample contamination, based on debris and sample color, was made. Titration was performed on a sample aliquot of 1 ml diluted to a volume of 5 ml using distilled water. The titrant used was 0.1N NaOH. Total gastric acid output in the stomach was determined by titration to pH 7. A dose of 300 mg/kg p.o. of the compound was administered to a group of rats and its effect on the volume of gastric secretion and acid output compared to a control group receiving 0.5% Methocel p.o. The activity of the compound is set forth in Table I.

TABLE I

| Dose mg/kg | Volume of Gastric Secretions | Gastric Acid Output |
|---|---|---|
| 300 | 53 | 38.8 |

The method currently preferred for the preparation of this compound is illustrated in the following example:

EXAMPLE I

A. 1-(4-Chlorophenyl)-3-nitroso-2-imidazolidinone

In a solution of glacial acetic acid (2750 ml) and water (250 ml) was dissolved 150 g (0.75 mol) of 1-(4-chlorophenyl)-2-imidazolidinone with heating. The solution was cooled to room temperature, and sodium nitrite (70 g, 1.0 mol) in water (200 ml) was added dropwise over 1 hour. The mixture was stirred for another 6 hours, diluted with water (1.5 l.) and the product (137 g, 81%) was collected, m.p. 154°–156°.

B. 1-Amino-3-(4-chlorophenyl)-2-imidazolidinone sulfate

To a solution of dioxane (1 l.) and 4N $H_2SO_4$ (1 l.) was added 113 g (0.50 mol) of A. The creamy yellow mixture was cooled and maintained at about 10° and zinc powder (65 g) was added in portions over 1.5 hour. The mixture was stirred another 24 hours and then filtered. The collected solid was set aside. The filtrate was diluted with water to yield more solid. This material was recrystallized from water (10 l.) to yield 22 g after filtration to remove recovered A. The solid which had been set aside was recrystallized from 50% aq. ethanol (v/v, 8 l.) to yield another 13 g of B, a yield of 27%.

An analytical sample, m.p. 241°–245°, was obtained by recrystallization from alcohol.

Anal. Calcd. for $C_9H_{10}ClN_3O.\frac{1}{2} H_2SO_4$: C, 41.73; H, 4.25; N, 16.12. Found: C, 41.37; H, 4.22; N, 16.26.

C. 1-(4-Chlorophenyl)-3-ureido-2-imidazolidinone

A 42.3 g (0.167 mole) sample of B. was suspended in 560 ml glacial acetic acid. A solution of potassium cyanate (264 g, 0.326 mole) in 80 ml $H_2O$ was added to the mixture and the resulting solution was stirred and refluxed for 15 hours, cooled, and diluted with 4000 ml $H_2O$. The mixture was stirred for 45 min. and the solid was filtered, washed with 200 ml $H_2O$, air dried, and then dried at 100° for 3 hours to give 31.5 g (76%) of the product, m.p. 212°–216°. An analytical sample, m.p. 237°–240°, was obtained by recrystallization from acetonitrile.

Anal. Calcd. for $C_{10}H_{11}ClN_4O_2$: C, 47.15; H, 4.36; N, 21.99. Found: C, 47.27; H, 4.36; N, 22.06.

What is claimed is:

1. The compound 1-(4-chlorophenyl)-3-(ureido)-2-imidazolidinone.